(12) United States Patent
Nakashima

(10) Patent No.: US 10,267,749 B2
(45) Date of Patent: Apr. 23, 2019

(54) INSPECTION METHOD

(71) Applicant: NuFlare Technology, Inc., Yokohama-shi (JP)

(72) Inventor: Kazuhiro Nakashima, Kawasaki (JP)

(73) Assignee: NuFlare Technology, Inc., Yokohama-shi (JP)

( * ) Notice: Subject to any disclaimer, the term of this patent is extended or adjusted under 35 U.S.C. 154(b) by 0 days.

(21) Appl. No.: 15/926,004

(22) Filed: Mar. 20, 2018

(65) Prior Publication Data
US 2018/0306733 A1    Oct. 25, 2018

(30) Foreign Application Priority Data

Apr. 21, 2017    (JP) ................. 2017-084618

(51) Int. Cl.
| | | |
|---|---|---|
| *G01N 21/00* | (2006.01) | |
| *G01N 21/956* | (2006.01) | |
| *G01N 21/88* | (2006.01) | |

(52) U.S. Cl.
CPC ... *G01N 21/95607* (2013.01); *G01N 21/8806* (2013.01); *G01N 2021/95676* (2013.01)

(58) Field of Classification Search
CPC ........... G01N 21/956; G01N 21/95607; G01N 21/8806; G01N 2021/95676; G06T 7/001; G06T 2207/30148
USPC ..................................................... 356/237.2
See application file for complete search history.

(56) References Cited

U.S. PATENT DOCUMENTS

| | | | | |
|---|---|---|---|---|
| 7,514,660 | B2* | 4/2009 | Ikeda | ...................... G02B 7/08 |
| | | | | 250/201.2 |
| 8,760,642 | B2 | 6/2014 | Hori et al. | |
| 9,922,415 | B2* | 3/2018 | Inoue | ...................... G06T 7/001 |
| 2002/0053634 | A1* | 5/2002 | Watanabe | ............. B82Y 10/00 |
| | | | | 250/201.2 |
| 2017/0206433 | A1* | 7/2017 | Ogawa | ...................... G06T 7/74 |
| 2018/0003649 | A1* | 1/2018 | Otaki | ............... G01N 21/95607 |
| 2018/0114306 | A1* | 4/2018 | Ogawa | ............... G02B 21/0092 |

FOREIGN PATENT DOCUMENTS

| | | |
|---|---|---|
| JP | 2012-237687 | 12/2012 |

* cited by examiner

*Primary Examiner* — Hoa Q Pham
(74) *Attorney, Agent, or Firm* — Oblon, McClelland, Maier & Neustadt, L.L.P.

(57) ABSTRACT

Provided is an inspection method including: irradiating a sample to be inspected with illuminating light; acquiring a first image of the sample to be inspected, with an auto focuser using the illuminating light reflected from the sample to be inspected; storing autofocus function coordinates acquired with the auto focuser in the acquiring the first image; calculating a two-dimensional polynomial approximation of the autofocus function coordinates; and controlling focusing in acquiring a second image of the sample to be inspected, with the two-dimensional polynomial approximation.

12 Claims, 7 Drawing Sheets

INSPECTION METHOD

CROSS-REFERENCE TO RELATED APPLICATION

This application is based upon and claims the benefit of priority from Japanese Patent Applications No. 2017-084618, filed on Apr. 21, 2017, the entire contents of which are incorporated herein by reference.

FIELD OF THE INVENTION

Embodiments described herein relate generally to an inspection method. The present disclosure relates to, for example, an inspection method of inspecting a pattern with acquisition of an optical image of a pattern image by irradiating a sample to be inspected, such as a mask used in manufacturing a semiconductor element, with a laser beam.

BACKGROUND OF THE INVENTION

Recently, a demand for precision management of a circuit line width required for semiconductor elements has been increasingly high. A reduced projection lithography device referred to as a so-called stepper exposes and transfers a pattern onto a wafer with an original pattern including a circuit pattern formed (also referred to a photolithography mask or a reticle, and, hereinafter, collectively referred to as a mask) to form a circuit, so that the semiconductor elements are manufactured. Therefore, a pattern drawing apparatus using an electron beam capable of drawing a fine circuit pattern is used in order to manufacture the mask for transferring the fine circuit pattern onto the wafer. The pattern drawing apparatus may be used to directly draw a pattern circuit onto a wafer.

Improvement in yield is necessary for the manufacture of LSI, such as a central processing unit (CPU) or a field programmable gate array (FPGA), involving significant manufacturing costs. One main factor that causes the yield to be reduced is a pattern defect of a mask used in exposing and transferring an ultra-fine pattern onto a semiconductor wafer with a photolithography technique. Recently, a scale required to be detected as a pattern defect has been considerably small as an LSI pattern scale to be formed on a semiconductor wafer has been miniaturized. Therefore, a pattern inspection apparatus that inspects a defect of a transferring mask used in manufacturing LSI desirably increases in precision.

A method of performing inspection by comparing an optical image including a pattern formed on a sample, such as a photolithography mask, captured at a predetermined magnification with a magnification optical system, to designed pattern data or an optical image including a pattern of the same kind on the sample, captured, has been known as an inspection method. Examples of a pattern inspection method include "die to die inspection" including: comparing pieces of optical image data each including a pattern of the same kind captured at a different position on the same mask, and "die to database inspection" including: inputting drawing data (pattern data) including pattern-designed CAD data converted into an apparatus input format to be input into a drawing apparatus in drawing a pattern onto a mask, into an inspection apparatus; generating designed image data (a reference image) based on the drawing data; and comparing an optical image including the pattern captured, being measurement data, to the designed image data. In the inspection method in the inspection apparatus, a sample is mounted on a stage and then the stage moves, so that a light beam scans on the sample and the inspection is performed. A light source and an illuminating optical system irradiate the sample with the light beam. Light transmitted through or reflected from the sample forms an image on a photodetector through an optical system. The image captured by the photodetector is transmitted as measurement data to a comparative circuit. The comparative circuit compares the measurement data and the reference data in accordance with an appropriate algorithm after positioning between the images, and determines that a pattern defect is present when inconsistency is acquired.

SUMMARY OF THE INVENTION

An inspection method according to an embodiment includes: irradiating a sample to be inspected with illuminating light; acquiring a first image of the sample to be inspected, with an auto focuser using the illuminating light reflected from the sample to be inspected; storing autofocus function coordinates acquired with the auto focuser in the acquiring the first image; calculating a two-dimensional polynomial approximation of the autofocus function coordinates; and controlling focusing in acquiring a second image of the sample to be inspected, with the two-dimensional polynomial approximation.

DETAILED DESCRIPTION OF THE EMBODIMENTS

Embodiments of the present disclosure will be described with reference to the drawings.

Note that a photolithography mask (a sample to be inspected) will be simply expressed as a mask in the following descriptions.

First Embodiment

An inspection method according to the present embodiment includes: irradiating a sample to be inspected with illuminating light; acquiring a first image of the sample to be inspected, with an auto focuser using the illuminating light reflected from the sample to be inspected; storing autofocus function coordinates acquired with the auto focuser in the acquiring the first image; calculating a two-dimensional polynomial approximation of the autofocus function coordinates; and controlling focusing in acquiring a second image of the sample to be inspected, with the two-dimensional polynomial approximation.

Figure 1:
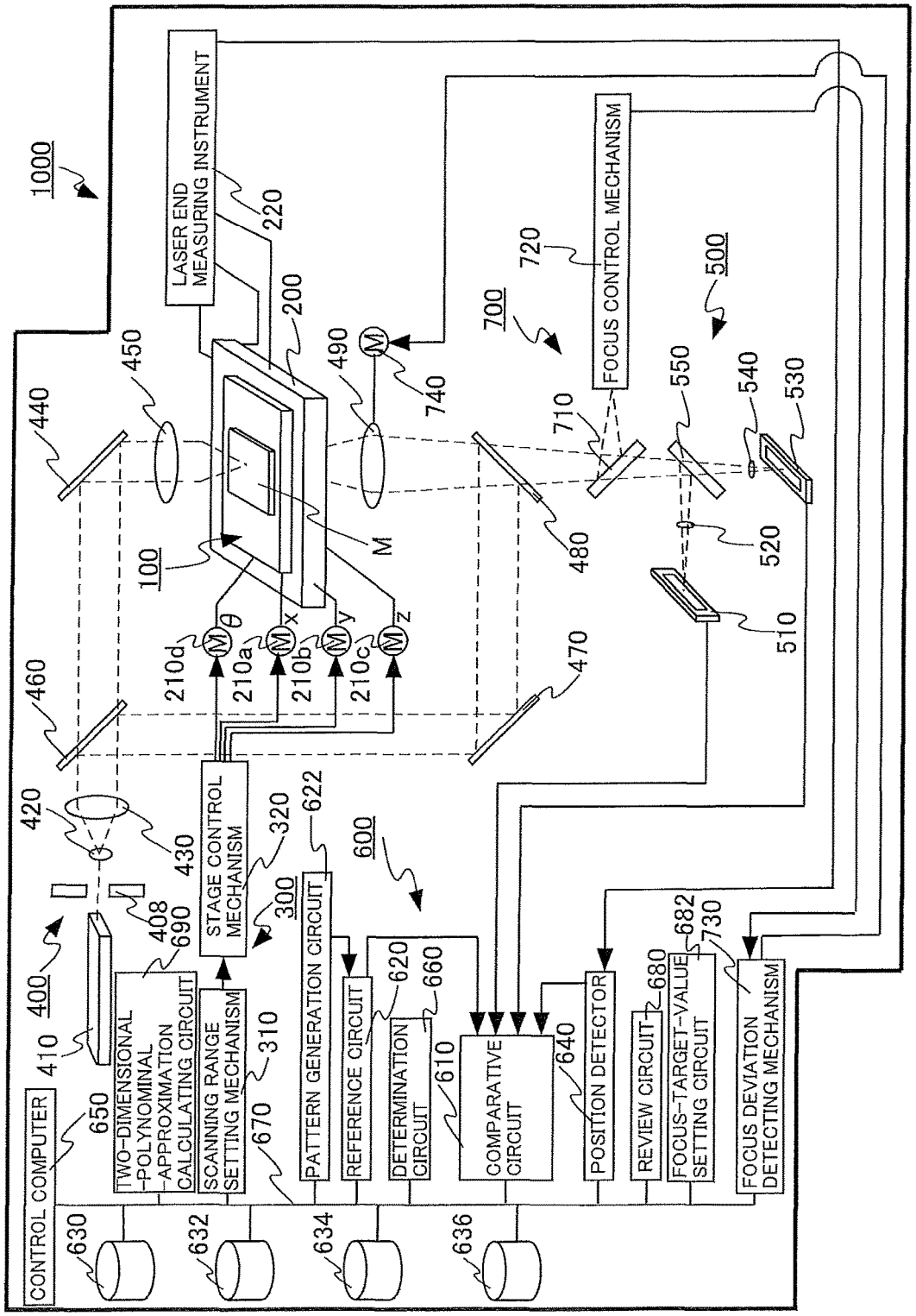
FIG. 1 is a schematic diagram of an inspection apparatus according to a first embodiment.

FIG. 1 is a schematic diagram of an inspection apparatus 1000 according to the present embodiment. The inspection apparatus 1000 according to the present embodiment is a pattern inspection apparatus that performs defect inspection to a mask M.

The mask M is mounted on a holder 100.

A stage 200 is disposed under the holder 100, supporting the holder 100. The stage 200 is moved in an X direction and a Y direction being lateral directions orthogonal to each other by a first stage-controller 210a and a second stage-controller 210b, respectively. The stage 200 is moved in a Z direction perpendicular to the X direction and the Y direction by a third stage-controller 210c. Furthermore, the stage 200 is rotated in a plane perpendicular to the Z direction by a fourth stage-controller 210d. Note that the first stage-controller 210a, the second stage-controller 210b, the third stage-controller 210c, and the fourth stage-controller 210d each are, for example, a publicly known motor or a piezoelectric element.

A laser end-measuring instrument 220 measures the position of the stage 200 in the X, Y, and Z directions. The position of the stage 200 that has been measured is input into a position detector 640 to be described later.

A movement control mechanism 300 includes a scanning range setting mechanism 310 connected to a control computer 650 to be described later through a bus line 670, and a stage control mechanism 320 that controls the first stage-controller 210a, the second stage-controller 210b, the third stage-controller 210c, and the fourth stage-controller 210d to move the stage 200 in a scanning range set with the scanning range setting mechanism 310.

An illuminator 400 includes an aperture stop 408, a light source 410, a first lens for the illuminator 420, a second lens for illuminator 430, a first mirror for the illuminator 440, a condenser lens 450, a first light-beam-splitter for the illuminator 460, a second mirror for the illuminator 470, a second light-beam-splitter for the illuminator 480, and an objective lens 490.

Illuminating light, such as a laser beam, emitted from the light source 410 passes through the aperture stop 408, and then is expanded to be a parallel light beam by the first lens for the illuminator 420 and the second lens for the illuminator 430. The aperture stop 408 adjusts the diameter of the light beam, namely, the numerical aperture (NA). The upper surface of the mask M is irradiated with the light beam that has been expanded by the first mirror for the illuminator 440 and the condenser lens 450. The first lens for the illuminator 420, the second lens for the illuminator 430, the first mirror for the illuminator 440, and the condenser lens 450 are included in a transmissive illuminating system.

Note that, since the mask M can be inspected close to a state where exposure is performed with the mask M, the wavelength of the light source 410 is desirably substantially the same as the wavelength of a light source included in a lithography device using the mask M.

The illuminating light, such as the laser beam, emitted from the light source 410 passes through the aperture stop 408 and is expanded to be the parallel light beam by the first lens for the illuminator 420 and the second lens for the illuminator 430, and then is reflected by the first light-beam-splitter for the illuminator 460 disposed between the second lens for the illuminator 430 and the first mirror for the illuminator 440. The lower surface of the mask M is irradiated with the illuminating light reflected by the first light-beam-splitter for the illuminator 460, by the second mirror for the illuminator 470 and the second light-beam-splitter for the illuminator 480. The first light-beam-splitter for the illuminator 460, the second mirror for the illuminator 470, and the second light-beam-splitter for the illuminator 480 are included in a reflective illuminating system.

Note that, specifically, a semi-transparent mirror, a slit, and a polarizing beam splitter can be favorably used as the first light-beam-splitter for the illuminator 460 and the second light-beam-splitter for the illuminator 480.

An image forming unit 500 includes a first photodetector 510, a first lens for the image forming unit 520, a second photodetector 530, a second lens for the image forming unit 540, and a separating mirror 550.

The illuminating light applied to the upper surface of the mask M by the transmissive illuminating system to pass through the mask M is referred to as transmitted light. The illuminating light applied to the lower surface of the mask M by the reflective illuminating system to reflect from the mask M is referred to as reflected light. The transmitted light and the reflected light are incident on the separating mirror 550 through the objective lens 490 and the second light-beam-splitter for the illuminator 480. The transmitted light forms an image on the first photodetector 510 through the first lens for the image forming unit 520 from the separating mirror 550. The reflected light forms an image on the second photodetector 530 through the second lens for the image forming unit 540 from the separating mirror 550.

A controller 600 includes a comparative circuit 610, a reference circuit 620, a pattern generation circuit 622, a pattern-data storage unit 630, an autofocus-function-coordinates storage unit 632, a two-dimensional-polynomial-approximation storage unit 634, an image storage unit 636, a position detector 640, the control computer 650, a determination circuit 660, the bus line 670, a review circuit 680, a focus-target-value setting circuit 682, and a two-dimensional-polynomial-approximation calculating circuit 690.

An autofocus mechanism 700 includes an autofocus light beam splitter 710, a focus deviation detecting mechanism 720, a focus control mechanism 730, and a motor for the autofocus mechanism 740. The autofocus mechanism is an example of the auto focuser.

The autofocus light beam splitter 710 inputs the reflected light into the focus deviation detecting mechanism 720. The focus deviation detecting mechanism 720 detects the degree of focus deviation from the reflected light that has been input, and inputs the degree of focus deviation into the focus control mechanism 730. On the basis of the degree of focus deviation that has been input, the focus control mechanism 730 controls the motor for the autofocus mechanism 740 to move the objective lens 490 in the height direction, so that the objective lens 490 is focused on the mask M. Note that moving the stage 200 in the Z direction with the third stage-controller 210c may focus the objective lens 490 on the mask M.

Specifically, a semi-transparent mirror, a slit, and a polarizing beam splitter can be favorably used as the autofocus light beam splitter 710.

Figure 2B:
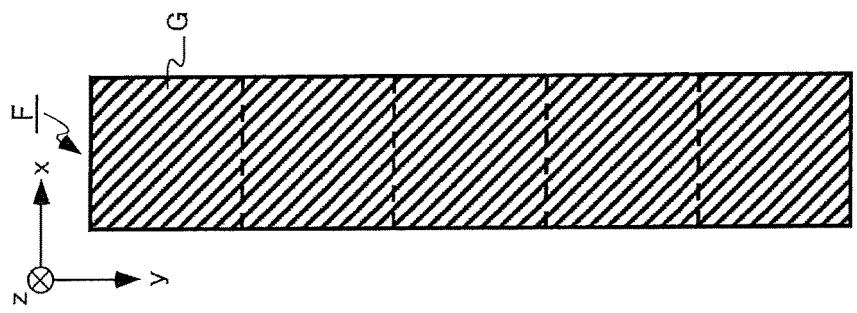
FIGS. 2A and 2B are schematic diagrams for describing an inspection method of a sample to be inspected (a mask) according to the first embodiment.
Figure 2A:
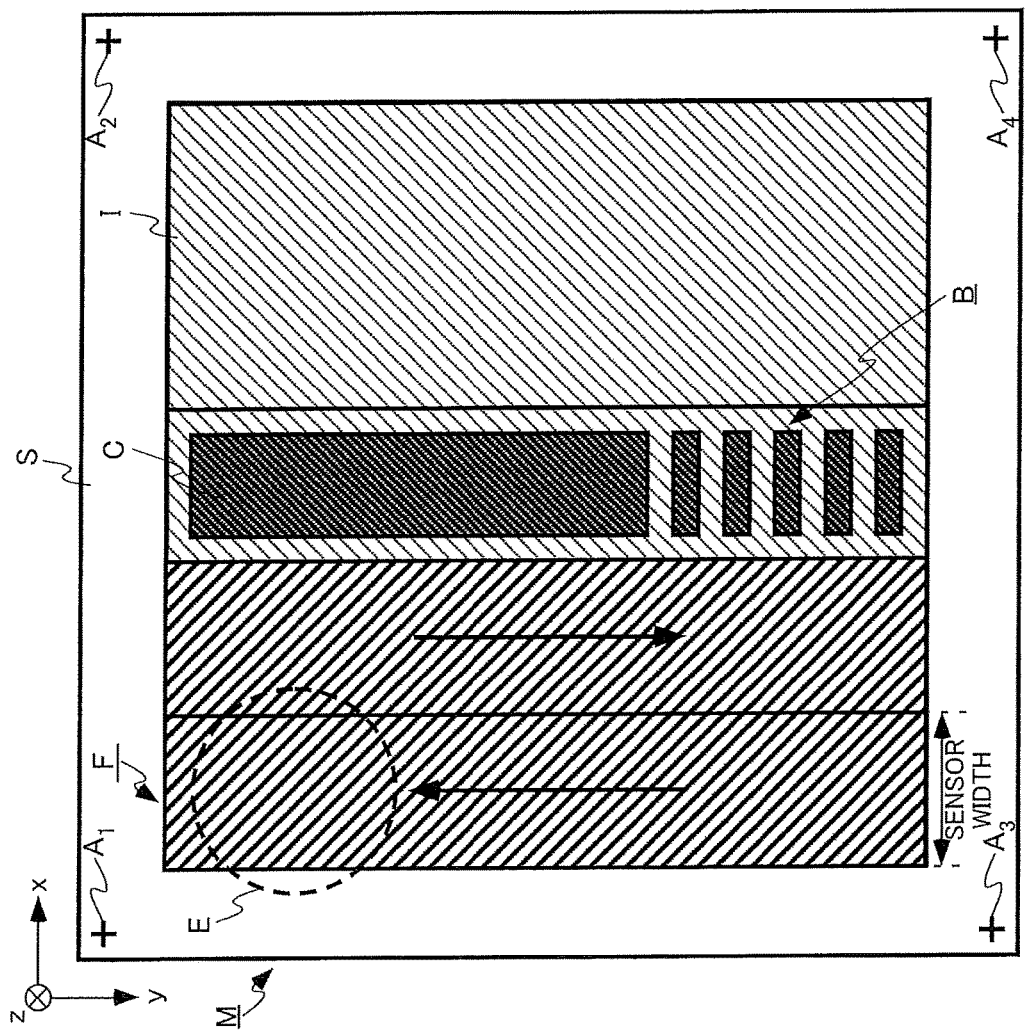

FIGS. 2A and 2B are schematic diagrams for describing an inspection method of a mask according to the present embodiment. FIG. 2A is a schematic diagram of the mask M to be inspected according to the present embodiment.

The mask M has a region to be inspected I provided on a substrate S. For example, the substrate S is formed of quartz. Patterns, such as a line-and-space pattern B and a solid pattern C, are disposed in the region to be inspected I. "Solid pattern" is a portion including no pattern present inside an optical visual field E during scanning.

As the inspection method of the mask M, for example, the stage 200 drives along the Y axis to pass the region to be inspected I into the optical visual field E, and then a strip-shaped region image F having the sensor width of the first photodetector 510 or the second photodetector 530 is acquired. Next, the stage 200 moves at a predetermined pitch along the X axis. Next, the stage 200 drives along the Y axis, so that a region image at a different portion of the region to be inspected I is acquired. This processing is repeated to acquire the entire region image of the region to be inspected I.

FIG. 2B is a schematic diagram illustrating an inspection method of the region image F. The comparative circuit 610 divides the region image F that has been acquired into a plurality of processing blocks G. Then, comparison is performed for each processing block G.

Note that, during the comparison, it is determined whether a pattern of the same kind is present, on the basis of the number of pairs of edges in an XY plane and an average line width in the XY plane in the image of the processing block G. Then, when the number of edges in each of the X direction and the Y direction is close to zero, it is determined that a solid pattern is present. Alternatively, it is determined that no pattern is present in the optical visual field, on the basis of no pattern present in the image of the processing block G.

Note that the inspection method of the mask M is not limited to the above description.

Figure 3:
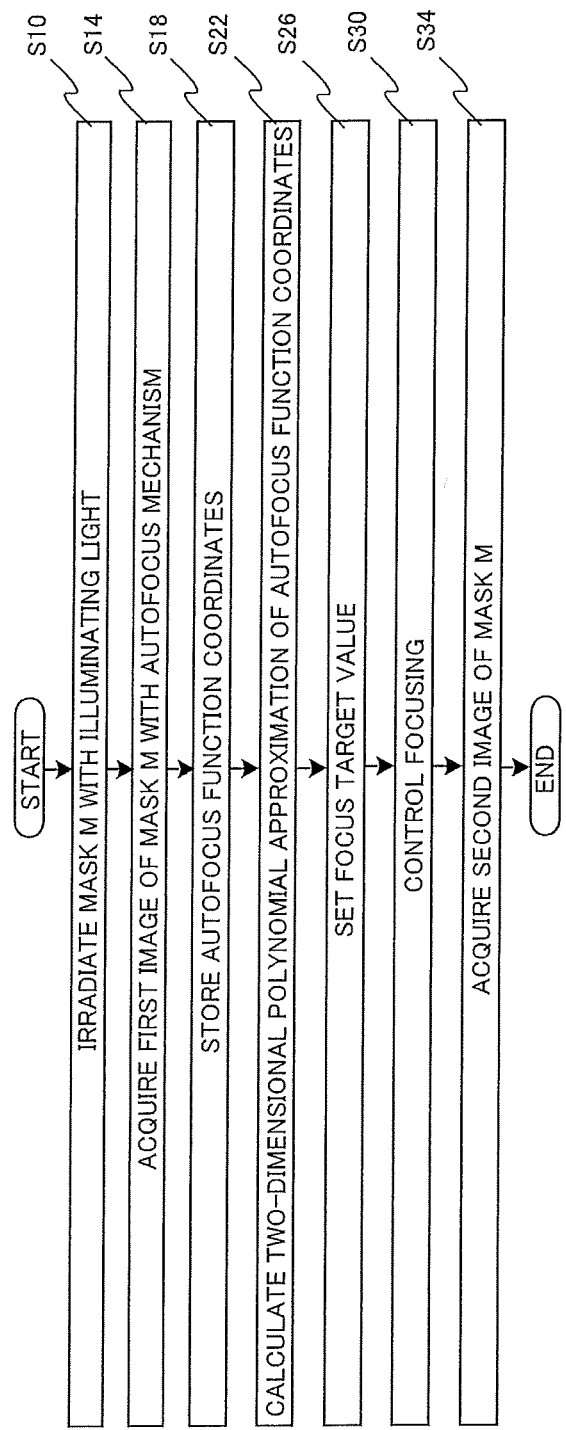
FIG. 3 is a flowchart of the inspection method according to the first embodiment.

FIG. 3 is a flowchart of the inspection method according to the present embodiment.

First, the illuminator 400 irradiates the mask M with the illuminating light (S10). The image forming unit 500 acquires, as a first image, an image formed with the illuminating light transmitted through the mask M or an image formed with the illuminating light reflected from the mask M (S14). Here, the autofocus mechanism 700 controls focusing in acquiring the first image. The first image that has been acquired is stored in the image storage unit 636. The first image is input into the comparative circuit 610.

The displacement of the objective lens 490 in the height direction or the displacement of the stage 200 in the Z direction at predetermined X and Y coordinates on the mask M is stored as autofocus function coordinates into the autofocus-function-coordinates storage unit 632 (S18).

Figure 4C:
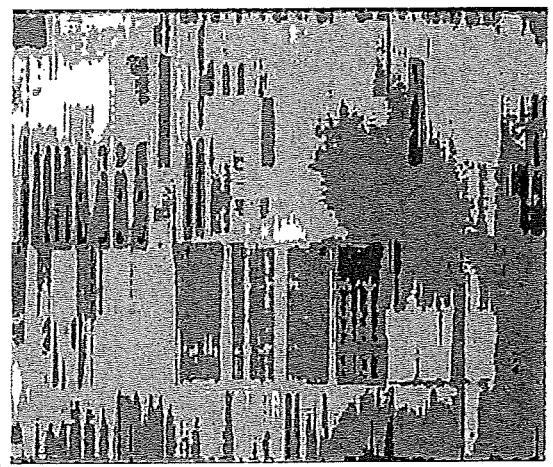
FIGS. 4A to 4C are maps of autofocus function coordinates according to the first embodiment.
Figure 4B:
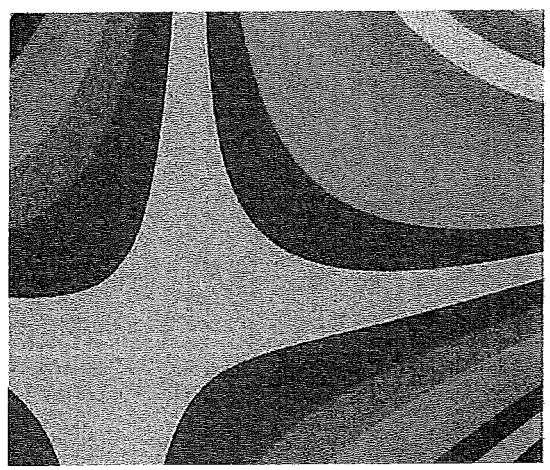
Figure 4A:
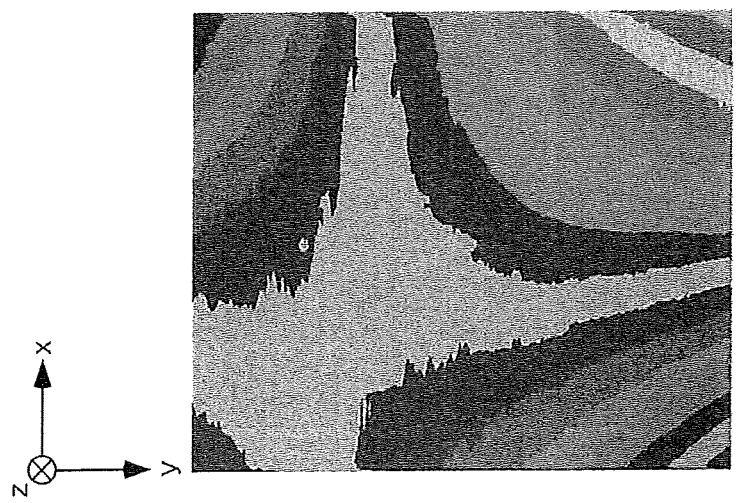

FIGS. 4A to 4C are maps illustrating the autofocus function coordinates according to the present embodiment. FIG. 4A is a map illustrating the autofocus function coordinates measured on the mask M, with contours.

Next, designed pattern data stored in the pattern-data storage unit 630 is input into the pattern generation circuit 622, and pattern generation is performed for each layer. The designed pattern data is previously created by a designer. Here, the designed pattern data is typically not designed to be directly read by the inspection apparatus 1000. Therefore, the designed pattern data is first converted into intermediate data created for each layer. The intermediate data is converted into data in a format to be directly read by the inspection apparatus 1000, and then the data is input into the pattern generation circuit 622.

Next, the reference circuit 620 creates a reference image as a reference for the first image from the pattern data generated for each layer by the pattern generation circuit 622. The reference image that has been created is input into the comparative circuit 610.

Next, the comparative circuit 610 compares the first image and the reference image. Here, a method of comparing the light quantity at a pattern portion of the first image and the light quantity at the corresponding pattern portion of the reference image is provided as exemplary comparison.

Note that a portion determined as a defect, as a result of the comparison, may be sent to the review circuit 680 and then an operator may review the portion. Here, the review is referred to as work in which the operator visually identifies and rechecks the defective portion detected by the inspection apparatus 1000.

Next, the two-dimensional-polynomial-approximation calculating circuit 690 calculates a two-dimensional polynomial approximation of the autofocus function coordinates (S22). The two dimensional polynomial approximation that has been created is stored into the two-dimensional-polynomial-approximation storage unit 634. Note that, when the two-dimensional polynomial approximation is calculated, the entirety of the autofocus function coordinates acquired at the predetermined pitch in the performance of the inspection may be used or part of the acquired autofocus function coordinates may be used.

FIG. 4B illustrates the autofocus function coordinates illustrated in FIG. 4A, approximated with the two dimensional polynomial approximation, with contours. FIG. 4C illustrates the difference between FIGS. 4A and 4B. The pattern of the difference occurs depending on a pattern shape formed on the mask M.

Next, the focus-target-value setting circuit 682 sets, as a focus target value, the displacement of the objective lens 490 in the height direction or the displacement of the stage 200 in the Z direction necessary for the focus control, with the two dimensional polynomial approximation that has been created (S26).

Next, the focus control mechanism 730 controls the displacement of the objective lens 490 in the height direction or the displacement of the stage 200 in the Z direction, on the basis of the focus target value (S30).

Next, the image forming unit 500 acquires, as a second image, an image formed with the illuminating light transmitted through the mask M or an image formed with the illuminating light reflected from the mask M (S34). Here, when transcription evaluation is performed, the second image is favorably the image formed with the illuminating light transmitted through the mask M.

With control of the aperture stop 408, a first numerical aperture in the acquisition of the first image is favorably made larger than a second numerical aperture in the acquisition of the second image.

Next, an operational effect according to the present embodiment will be described.

It is desirable to acquire an image formed with the illuminating light transmitted through the mask M, acquired with a small numerical aperture, as an image for the transcription evaluation. This is because, since the small numerical aperture decreases sensitivity, it can be determined whether the degree of a defect detected in the mask M has no influence on transcription.

For example, according to the present embodiment, the first image is acquired with the first numerical aperture to determine that the defect is present, and then the second image is acquired with the second aperture smaller than the first numerical aperture. Then, in a case where no defect is detected in the second image, it can be determined that the degree of the defect has no influence on the transcription.

In this case, use of 100% of the illuminating light generated from the light source 410 for the transmitted light allows an image acquisition time to be shortened.

However, the present autofocus mechanism 700 performs the focus control with the reflected light, as described above. Therefore, when the illuminating light generated from the light source 410 is used for the transmitted light, there is a problem that autofocus control cannot be performed.

In the inspection method according to the present embodiment, the two-dimensional polynomial approximation of the autofocus function coordinates is calculated, and then focusing in the acquisition of the second image of the mask M is controlled with the two-dimensional polynomial approximation. This arrangement allows the focusing to be controlled even when the reflected light is weak and the autofocus control cannot be performed.

The occurrence of the shape of the difference occurring in FIG. 4C, depending on the pattern shape formed on the mask M, shows that the autofocus function coordinates has pattern dependency. The use of the two dimensional polynomial approximation allows the pattern dependency of the autofocus function coordinates to be averaged, so that the focus control having less pattern dependency can be performed.

The inspection method according to the present embodiment can provide an inspection method of allowing the focus control having the less pattern dependency to be performed.

Second Embodiment

An inspection method according to the present embodiment is different from the inspection method according to the first embodiment in the following points. In storing autofocus function coordinates acquired with an autofocus mechanism in acquiring a first image, a reference image as a reference for the first image is compared to the first image. On the basis of the comparison, an effective portion of the first image is extracted and the autofocus function coordinates of the effective portion are stored. Here, the descriptions of points that duplicate with respect to the first embodiment will be omitted.

Figure 5:
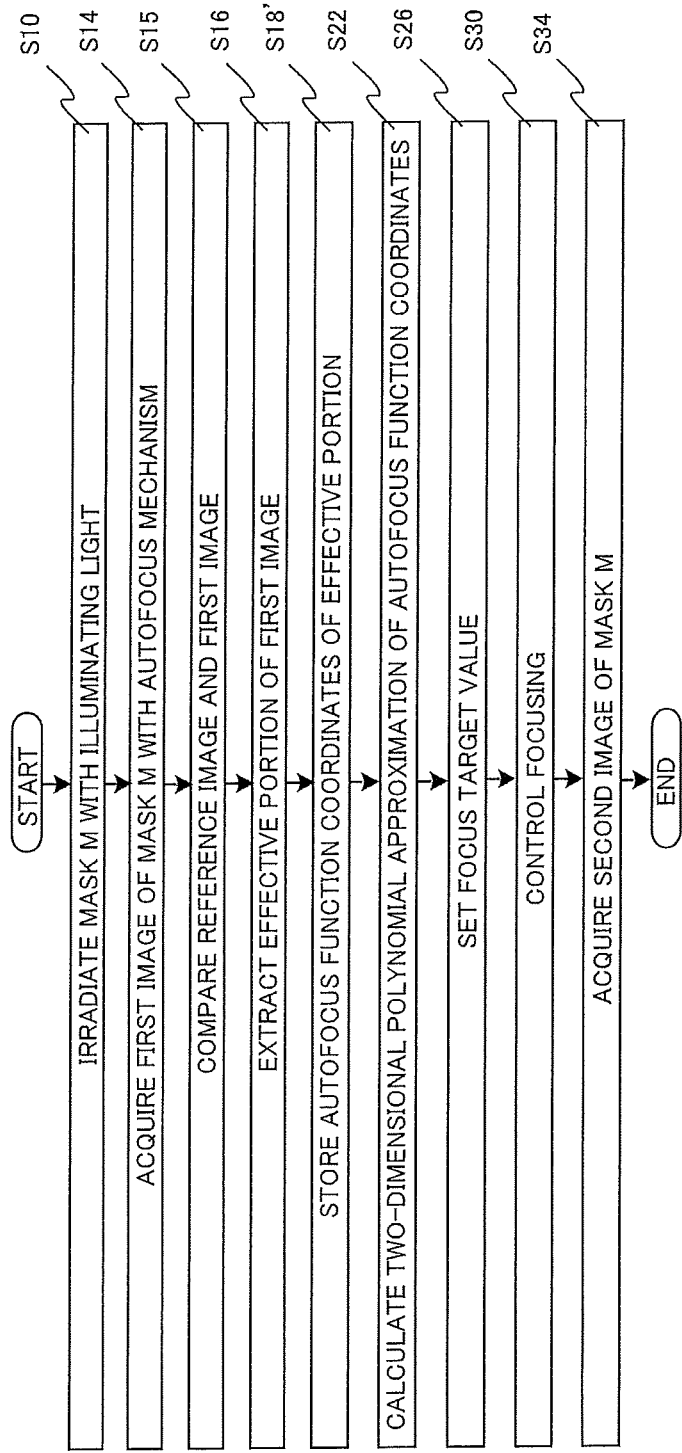
FIG. 5 is a flowchart of an inspection method according to a second embodiment.

FIG. 5 is a flowchart of the inspection method according to the present embodiment. The flowchart is different from the flowchart illustrated in FIG. 3 according to the first embodiment in that the reference image and the first image are compared to each other (S15), in that the effective portion of the first image is extracted (S16), and in that the autofocus function coordinates of the effective portion are stored (S18').

As illustrated in FIG. 4C, pattern dependency occurs in the autofocus function coordinates. A predetermined effective portion is extracted with the first image and then the autofocus function coordinates is stored, so that focus control having the pattern dependency of the autofocus function coordinates reduced can be performed.

The effective portion desirably includes, for example, a pattern of the same kind. This is because the pattern dependency of the autofocus function coordinates is further reduced. Here, for example, a determination method of the pattern of the same kind including a line-and-space pattern includes: acquiring an average pattern pitch from the number of edges in an image in a processing block G; and giving validity when the pattern pitch is within a specified range.

The pattern of the same kind is favorably a solid pattern. This is because the solid pattern remains the same in height in a Z direction and the focus control can be performed easier. Here, for example, a determination method of the solid pattern includes: comparing the reference image (a solid image) and the first image for each processing block G; and determining that the solid pattern is present when no defect is present (e.g., the integrated value of gradient absolute values is a specified value or less).

The inspection method according to the present embodiment can provide an inspection method of allowing the focus control having the less pattern dependency to be performed.

Third Embodiment

An inspection method according to the present embodiment is different from the inspection method according to the first embodiment in the following points. In acquiring a first image of a sample to be inspected with an autofocus mechanism using illuminating light reflected from the sample to be inspected, a necessary portion for calculating a two-dimensional polynomial approximation is extracted with designed pattern data of the sample to be inspected. The first image of the necessary portion of the sample to be inspected is acquired with the autofocus mechanism using the illuminating light reflected from the sample to be inspected. Here, the descriptions of points that duplicate with respect to the first and second embodiments will be omitted.

Figure 6:
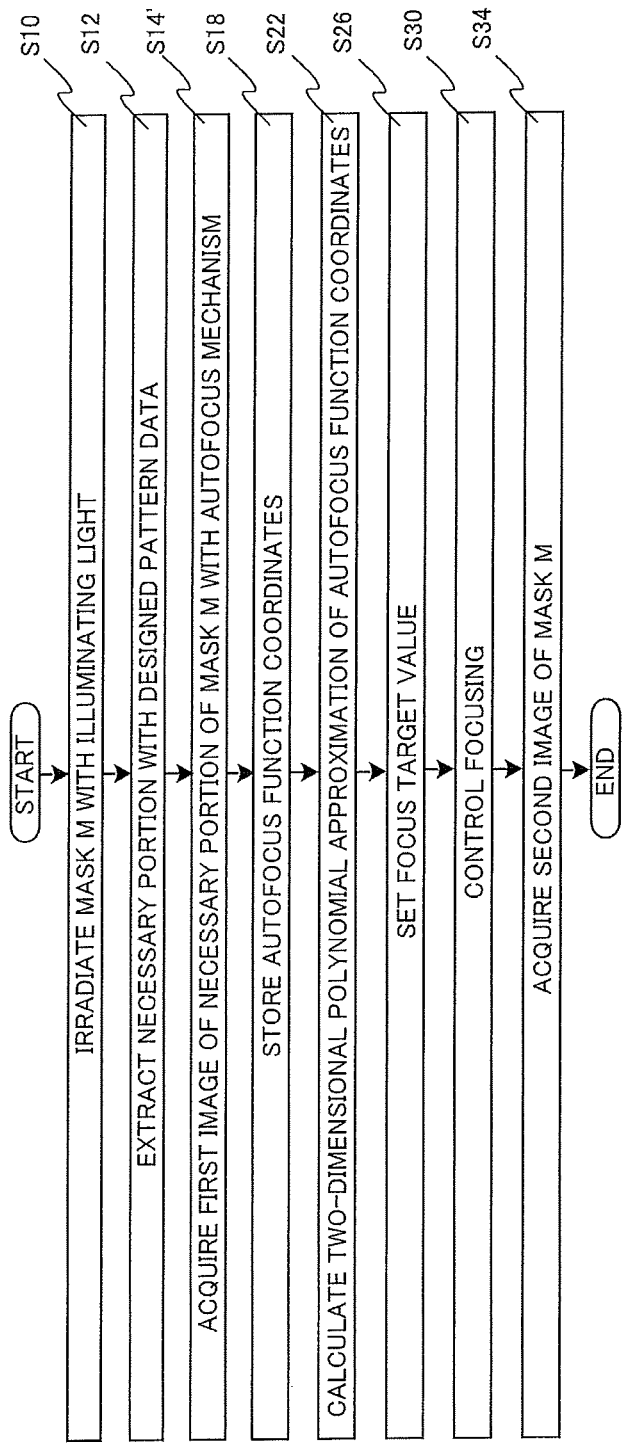
FIG. 6 is a flowchart of an inspection method according to a third embodiment.

FIG. 6 is a flowchart of the inspection method according to the present embodiment. The flowchart is different from the flowchart illustrated in FIG. 3 according to the first embodiment in that the necessary portion is extracted with the designed pattern data (S12) and in that the first image of the necessary portion of a mask M is acquired with the autofocus mechanism (S14').

In the inspection method according to the present embodiment, the necessary portion is previously extracted with the designed pattern data. Therefore, a time for acquiring the first image can be shortened. Note that inspection of the sample to be inspected according to the present embodiment can be performed in comparison between a second image and a reference image. The necessary pattern is favorably, for example, a pattern of the same kind. The pattern of the same kind is favorably a solid pattern.

The inspection method according to the present embodiment can provide an inspection method of allowing focus control having less pattern dependency to be performed.

Fourth Embodiment

An inspection method of the present embodiment is different from the inspection method according to the first embodiment in that a predetermined pattern cycle is acquired from a first image and in that the autofocus function coordinates of the coordinates of a portion having the predetermined pattern cycle is stored. Here, the descriptions of points that duplicate with respect to the first, second, and third embodiments will be omitted.

Figure 7:
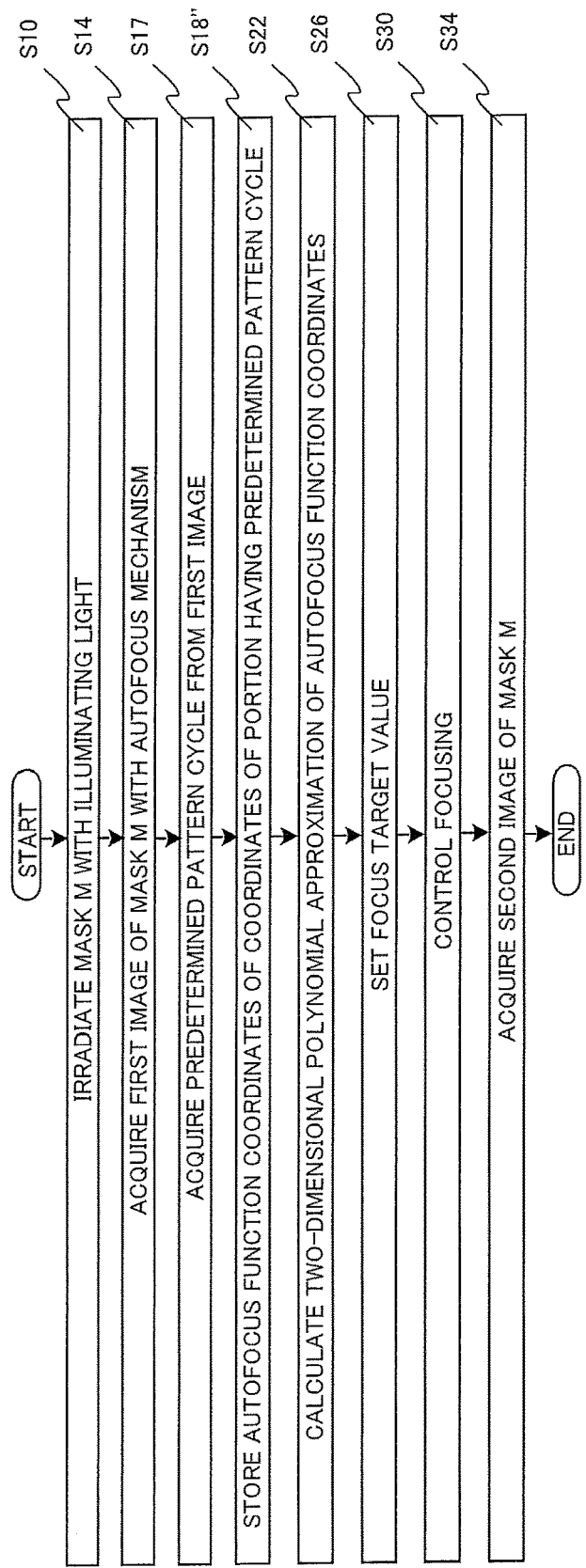
FIG. 7 is a flowchart of an inspection method according to a fourth embodiment.

FIG. 7 is a flowchart of the inspection method according to the present embodiment. The flowchart is different from the flowchart illustrated in FIG. 3 according to the first embodiment in that the predetermined pattern cycle is acquired from the first image (S17) and in that the autofocus function coordinates of the coordinates of the portion having the predetermined pattern cycle is stored (S18").

In the inspection method according to the present embodiment, a pattern cycle is acquired from the first image. Next, it is checked whether the pattern cycle that has been acquired is within the predetermined pattern cycle that has been previously determined. In this manner, the predetermined pattern cycle is acquired from the first image. Next, the autofocus function coordinates of the coordinates of the portion having the predetermined pattern cycle is stored.

In the inspection method according to the present embodiment, the acquisition of the predetermined pattern cycle allows focus control having the pattern dependency of the autofocus function coordinates reduced to be performed. Here, examples of the predetermined pattern cycle include a line-and-space pattern having a predetermined cycle.

The inspection method according to the present embodiment can provide an inspection method of allowing focus control having less pattern dependency to be performed.

In the descriptions above, the "units" each include a processing circuit or a processing apparatus, and the processing circuit includes an electric circuit, a computer, a processor, a circuit board, a quantum circuit, or a semiconductor apparatus. Each of the "units" may include a uniform processing circuit (the same processing circuit). Alternatively, a different processing circuit (an individual processing circuit) may be provided. A program for executing the processor is at least stored in a recording medium, such as a magnetic disk drive, a magnetic tape drive, an FD, or read only memory (ROM). The "mechanisms" each include a processing apparatus. The "storage units" or storage devices each include a recording medium, such as a magnetic disk drive, a magnetic tape drive, a FD, read only memory (ROM), or a solid state drive (SSD).

The embodiments of the present disclosure have been described above with reference to the specific examples. The embodiments are just exemplary, and the present disclosure is not limited to the embodiments. The constituent elements in each of the embodiments may be appropriately combined.

According to the embodiments, parts, such as apparatus configurations and manufacturing methods, not directly necessary for describing the present disclosure have been omitted, but a necessary apparatus configuration or manufacturing method can be appropriately selectively used. In addition, any inspection methods including an element of the present disclosure, appropriately altered in design by a person skilled in the art, are included in the scope of the present disclosure. The scope of the present disclosure is defined with the scope of the claims and the scope of equivalents of the claims.

What is claimed is:

1. An inspection method comprising:
   irradiating a sample to be inspected with illuminating light;
   acquiring a first image of the sample to be inspected, with an auto focuser using the illuminating light reflected from the sample to be inspected;
   storing autofocus function coordinates acquired with the auto focuser in the acquiring the first image;
   calculating a two-dimensional polynomial approximation of the autofocus function coordinates; and
   controlling focusing in acquiring a second image of the sample to be inspected, with the two-dimensional polynomial approximation.

2. The inspection method according to claim 1, further comprising:
   making a first numerical aperture in the acquisition of the first image of the sample to be inspected larger than a second numerical aperture in the acquisition of the second image of the sample to be inspected.

3. The inspection method according to claim 1, wherein the storing the autofocus function coordinates acquired with the auto focuser in the acquiring the first image includes
   comparing a reference image as a reference for the first image and the first image,
   extracting an effective portion of the first image, based on the comparing, and
   storing the autofocus function coordinates of the effective portion.

4. The inspection method according to claim 3, wherein the effective portion includes a pattern of the same kind.

5. The inspection method according to claim 4, wherein the pattern of the same kind is a solid pattern.

6. The inspection method according to claim 1, wherein the acquiring the first image of the sample to be inspected with the auto focuser using the illuminating light reflected from the sample to be inspected includes:
   extracting a necessary portion for calculating the two-dimensional polynomial approximation, with designed pattern data of the sample to be inspected; and
   acquiring the first image of the necessary portion of the sample to be inspected, with the auto focuser using the illuminating light reflected from the sample to be inspected.

7. The inspection method according to claim 6, wherein the necessary portion includes a pattern of the same kind.

8. The inspection method according to claim 7, wherein the pattern of the same kind is a solid pattern.

9. The inspection method according to claim 1, further comprising the acquiring the second image.

10. The inspection method according to claim 9, wherein the acquiring the second image includes using the illuminating light transmitted through the sample to be inspected.

11. The inspection method according to claim 10, wherein the acquiring the second image includes transmitting 100% of the illuminating light through the sample to be inspected.

12. The inspection method according to claim 1, further comprising:
   acquiring a predetermined cycle from the first image; and
   storing the autofocus function coordinates of coordinates of a portion having the predetermined pattern cycle.

* * * * *